US00PP36986P2

(12) United States Plant Patent
Evison

(10) Patent No.: US PP36,986 P2
(45) Date of Patent: Sep. 30, 2025

(54) ***CLEMATIS* PLANT NAMED 'EviGsy155'**

(50) Latin Name: ***Clematis patens* X *viticella***
Varietal Denomination: EviGsy155

(71) Applicant: Raymond J. Evison Ltd., Vale (GB)

(72) Inventor: Raymond J. Evison, Vale (GB)

(73) Assignee: RAYMOND J. EVISON LTD., Vale (GB)

( * ) Notice: Subject to any disclaimer, the term of this patent is extended or adjusted under 35 U.S.C. 154(b) by 0 days.

(21) Appl. No.: 19/182,744

(22) Filed: Apr. 18, 2025

(30) Foreign Application Priority Data

Nov. 27, 2024 (QZ) ..... PBR 20242812

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

*Primary Examiner* — Susan McCormick Ewoldt
(74) *Attorney, Agent, or Firm* — Penny J. Aguirre

(57) ABSTRACT

A new cultivar of *Clematis* plant named 'EviGsy155' that is characterized by its flowers that are large in size, its flowers that open purple-pink in color and mature to deep pink in color with red anthers, its flowers present from the base to the tip of the plant, its repeat flowering; blooming from May through July and re-blooming in September, its compact plant habit., its floriferous blooming habit, and its good suitability for use in gardens and in containers.

4 Drawing Sheets

CROSS REFERENCE TO A RELATED APPLICATION

This application claims priority to European Community Plant Variety Office (CPVO) Plant Breeder's Rights Application No. 2024/2812 filed on Nov. 27, 2024, the entire contents of which is incorporated by reference herein.

Botanical classification: *Clematis patens* X *viticella*.

Variety denomination: 'EviGsy155'.

BACKGROUND OF THE INVENTION

The present invention relates to a new and distinct cultivar of *Clematis* of hybrid origin and will be referred to hereafter by its cultivar name 'EviGsy155'. 'EviGsy155' is grown as an herbaceous climbing plant for use in the landscape or as a flowering potted plant for the terrace.

'EviGsy155' derived from an ongoing breeding program by the Inventor at his nursery in Guernsey, The Channel Islands. The goal of the breeding program is to select new cultivars of *Clematis* with a compact plant habits with an abundance of flowers that are large in size with unique flower colors and exhibit blooming from base to tip and repeat blooming. 'EviGsy155' was selected as a single unique plant in April of 2020 and arose from a controlled cross made in June of 2015 between unnamed and unpatented proprietary seedlings of *Clematis patens* X *viticella* from the Inventor's breeding program as both the female and male parents.

Asexual propagation of the new cultivar was first accomplished by stem cuttings under the direction of the Inventor in Guernsey, The Channel Islands in May of 2020. Asexual propagation by internodal stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'EviGsy155' as a unique cultivar of *Clematis*.

1. 'EviGsy155' exhibits flowers that are large in size.
2. 'EviGsy155' exhibits flowers that open purple-pink in color and mature to deep pink in color with red anthers.
3. 'EviGsy155' exhibits flowers present from the base to the tip of the plant.
4. 'EviGsy155' exhibits repeat flowering; blooming from May through July and re-blooming in September.
5. 'EviGsy155' exhibits a compact plant habit.
6. 'EviGsy155' exhibits a floriferous blooming habit.
7. 'EviGsy155' exhibits good suitability for use in gardens and in containers.

The female parent of 'EviGsy155' differs from 'EviGsy155' in having a taller plant height and light purple tepals. The male parent of 'EviGsy155' differs from 'EviGsy155' in having a less vigorous plant habit and light purple tepals. 'EviGsy155' can be most closely compared to the *Clematis* cultivars 'evipo077' (U.S. Plant Pat. No. 29,150) and 'evipo041' (U.S. Plant Pat. No. 24,171). Both 'evipo077' and 'evipo041' are similar to 'EviGsy155' in overall flower color. 'evipo077' differs from 'EviGsy155' in having in having a more vigorous growth and taller plant height and longer tepals that are light pink with a darker pink center stripe, and brown anthers. 'evipo041' differs from 'EviGsy155' in having bi-colored flowers with tepals that are more purple in color with darker pink center stripes and leaflets that are thinner and more lanceolate in shape.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102 (b) (1) for disclosures and/or sales that fall within a one-year grace period to the filing date. Disclosures include website listings by Raymond Evison Clematis, RHS Plants, Plantipp, Crocus, Floral Daily, IPM Essen, Waitrose Garden, Andrew W. Jeanes (LinkedIn), Hortweek, The Guernsey Clematis Nursery, AIPH, Horticulture Week, bloemen planten nieuws, Plantago, Gartenpraxis, GTN Xtra, and Geschlossener Ausstellerbereich,

BRIEF DESCRIPTION OF THE DRAWINGS

The accompanying color photographs illustrate the overall appearance and distinct characteristics of the new *Clematis*. The photographs were taken of a 1-year-old plant of 'EviGsy155' as grown in a 17-cm container in a conventional greenhouse in Guernsey, The Channel Islands. The photograph in FIG. 1 shows a side view of 'EviGsy155' in bloom.

The photograph in FIG. 2 provides a close-up view of the young flowers of 'EviGsy155'.

Figure 1:
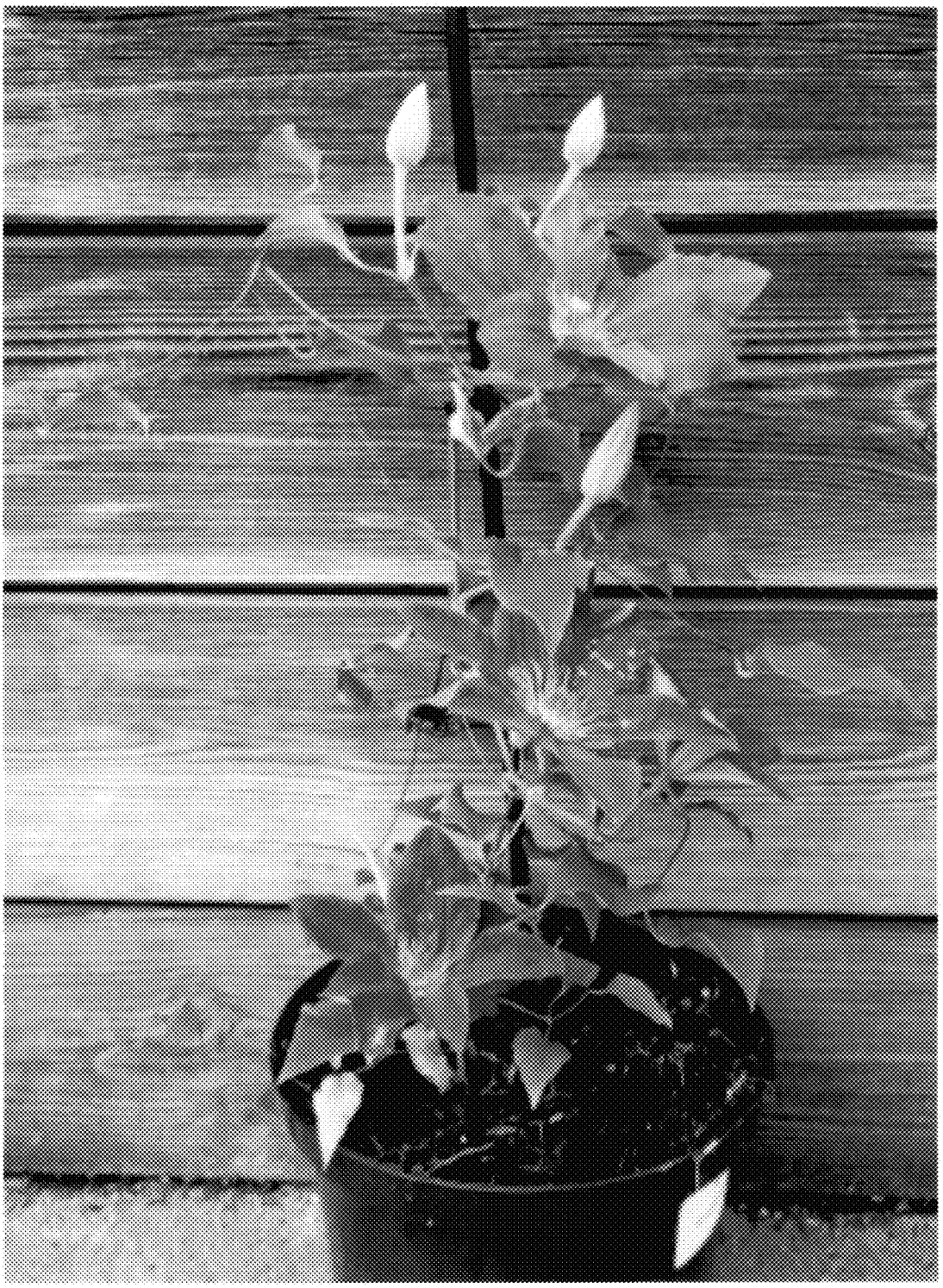
Figure 2:
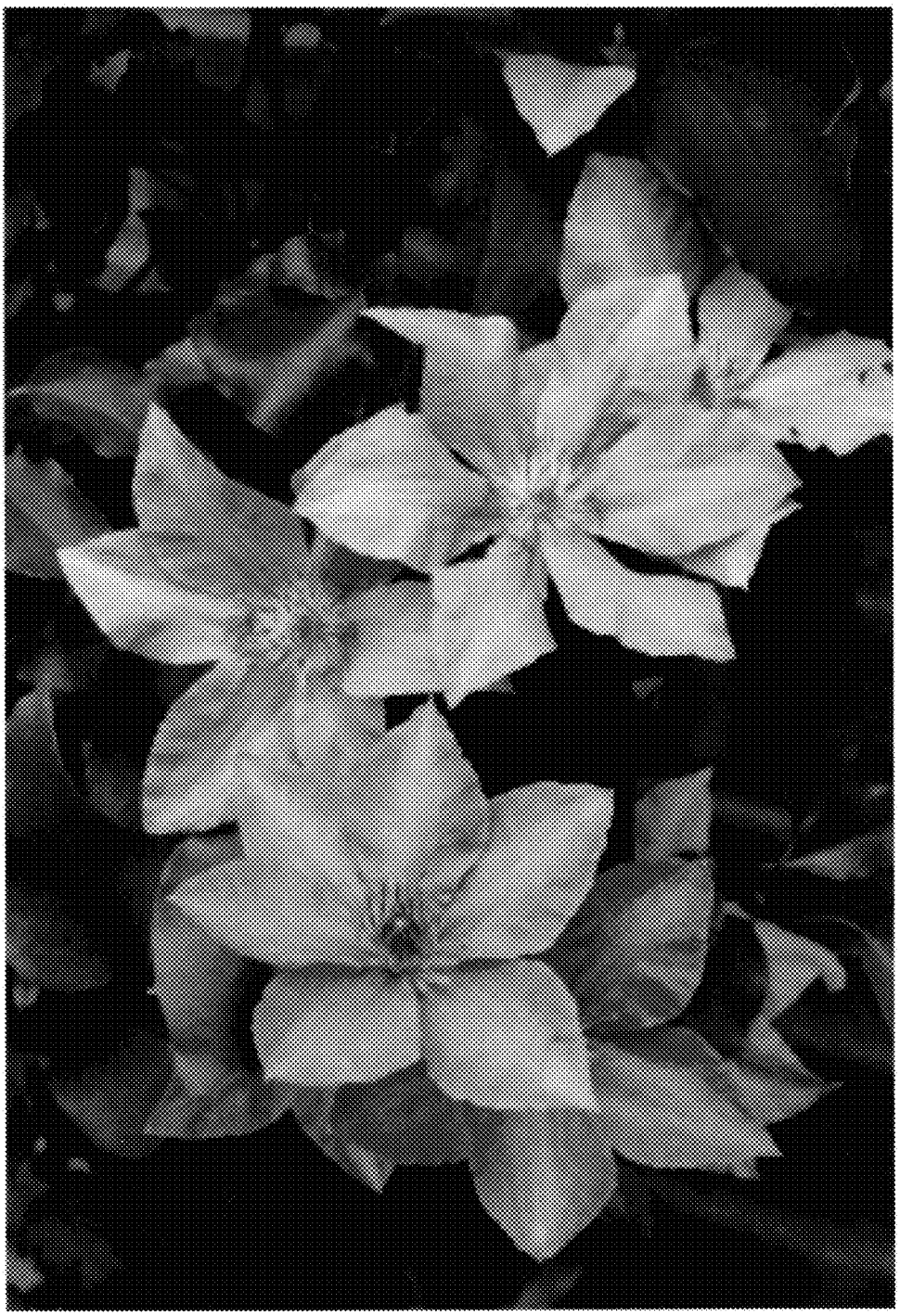
Figure 3:
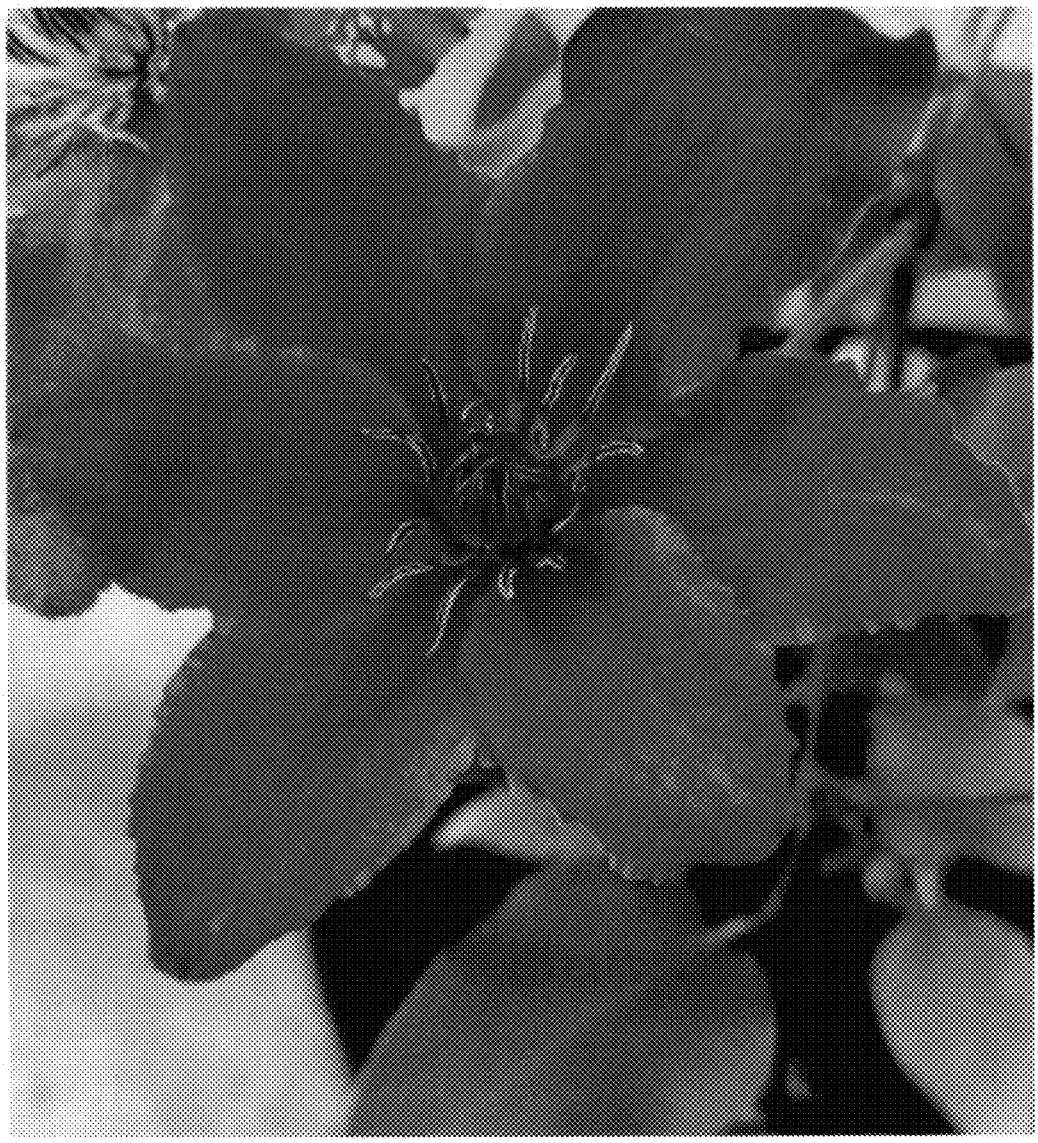

The photograph in FIG. 3 provides a close-up view of a mature flower of 'EviGsy155'.

Figure 4:
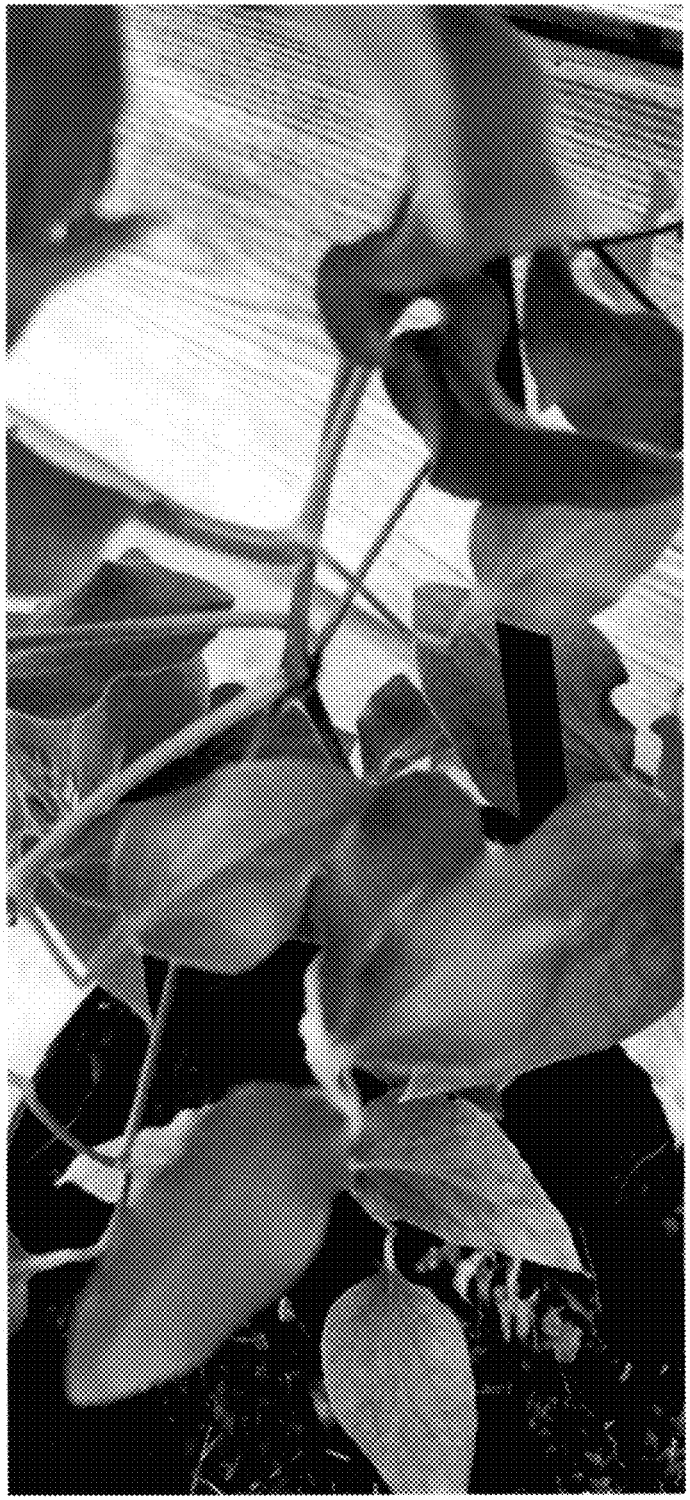

The photograph in FIG. 4 provides a close-up view of the foliage of 'EviGsy155'. The colors in the photographs are as close as possible with the digital photography techniques available, the color values cited in the detailed botanical description accurately describe the colors of the new *Clematis*.

DETAILED BOTANICAL DESCRIPTION

The following is a detailed description of 1-year-old plants of 'EviGsy155' as grown in 17-cm containers in Guernsey, The Channel Islands. The phenotype of the new cultivar may vary with variations in environmental, climatic, and cultural conditions, as it has not been tested under all possible environmental conditions. The color determination is in accordance with the 2015 Colour Chart of the Royal Horticultural Society, London, England, except where general color terms of ordinary dictionary significance are used.

General Description:

*Blooming period*.—Blooms from May to July and reblooms in late August and September in Guernsey, The Channel Islands.

*Plant type*.—Herbaceous woody vine, early blooming large flowering *Clematis*.

*Plant habit*.—Climber, blooms on new wood, compact.

*Height and spread*.—Average of 32 cm in height and 20 cm in width as a one-year-old plant as grown in a container, reaches 90 to 120 cm in height and width in one season as grown in the landscape.

*Hardiness*.—At least in U.S.D.A. Zones 5 to 9.

*Diseases*.—No susceptibility or resistance to pests and diseases has been observed.

*Root description*.—Fleshy.

*Propagation*.—Softwood cuttings from vegetative shoots.

*Time required for root initiation*.—Roots initiate in 3 to 4 weeks, another 4 to 6 weeks to produce a fully rooted cutting ready for potting, root development from plug to P7 is 3 to 6 months, 30 weeks to mature in a P12 container.

*Growth rate*.—Moderate.

*Vigor*.—Medium.

Stem Description:

*Shape*.—Round.

*Stem color*.—Young; 178A, mature; 178A, wood; 199A.

*Stem size*.—Length from base to flowering portion of the stem; 26 cm in length, diameter; 3 mm.

*Stem surface*.—Very sparsely pubescent.

*Stem strength*.—Strong.

*Internode length*.—Average of 6 cm.

*Branching*.—Basal branching.

Foliage Description:

*Leaf arrangement*.—Opposite, ternate.

*Leaf division*.—Compound.

*Leaf attachment*.—Petiolate.

*Leaf quantity*.—56 per stem, 3 leaflets per whole leaf.

*Leaf size*.—Average of 14 cm in length and 11 cm in width.

*Leaflet shape*.—Ovate.

*Leaflet base*.—Rounded to obtuse.

*Leaflet apex*.—Acute.

*Leaflet venation*.—Palmate, color; upper surface 145A, lower surface 144A to 144B.

*Leaflet margins*.—Entire.

*Leaflet attachment*.—Petiolule.

*Leaflet surface*.—Upper surface glabrous, glossy, lower surface matte.

*Leaflet size*.—Average of 5 cm in length and 2.8 cm in width.

*Leaflet color*.—Young upper and lower surface; 144A, mature upper and lower surface; 138B.

*Petioles*.—Up to 7 cm in length, 2 mm in width, 144A and 183B n color, sparsely pubescent surface.

*Petiolules*.—Up to 8 cm in length, 1.5mm in diameter, 144A to 144C in color and flushed with 183B, sparsely pubescent surface.

Inflorescence Description:

*Inflorescence type*.—Solitary; from one to 4 at upper axils.

*Inflorescence arrangement*.—Terminal and axillary on new growth.

*Pedicel*.—4 cm in length, 3 mm in diameter, 145A in color, glabrous surface, moderate strength.

*Bud description*.—Ovoid in shape, 3 cm in length, 1.3 cm in width, 145B to 145D in color, pubescent surface.

*Flower fragrance*.—None.

*Lastingness of flowers*.—Long lasting; individual flowers last about 14 days, self-cleaning.

*Flower quantity*.—5 open flowers, 3 buds.

*Flower type*.—Single, rotate, spreading, star-shaped.

*Flower aspect*.—Upward, rotate, held open in a tubular shape when opening and becomes flat as they mature.

*Flower size*.—Average of 12 cm in diameter (up to 14-cm) and 4 cm in depth.

*Tepal number*.—Varies between 9, 6, and 7.

*Tepal shape*.—Broadly elliptic to ovate.

*Tepal apex*.—Acuminate.

*Tepal base*.—Acute.

*Tepal margins*.—Entire with undulations.

*Tepal surface*.—Both surfaces glabrous, slightly satiny to matte.

*Tepal color*.—When opening upper surface; 72A and NN78A, midrib 78A, when opening lower surface; margins NN78A, midrib 78B to 78C, 145A in the middle, when fully open upper surface; 72B with hint of 72A and 78B, when fully open lower surface; 78C and 145B, margins NN78A, upper surface fading; 78B to 78C with hint of 72B, lower surface fading; 78C to 78D with 145C, margins NN78C, 78C to 78D with 145C.

*Tepal size*.—Average of 5.4 cm in length and 3.8 cm in width.

*Tepal arrangement*.—Overlapping.

*Tepal curvature in longitudinal section*.—Flat to moderately incurved.

*Receptacle*.—5 mm in depth, 4 mm in width, pubescent surface, round in shape, 145A to 145C in color.

Reproductive Organs:

*Gynoecium*.—Pistils; between 70 and 80, style; 1 cm in length, 1 mm in diameter, color 157D, stigma; slightly superior relative to the length of the filaments and height of the anthers, very small and hard to see, ovary; 145B in color.

*Androecium*.—Stamens; 150, filaments; 8 mm in length, glabrous surface, 157B to 157D in color, anthers; 7 mm in length, linear in shape, 80B to 80C in color, glabrous, pollen was not observed.

*Seed*.—Seed head; an average of 5.5 cm in length, 3.5 cm in width, shiny hairs, style; plumose at base, color; 143A to 147C, seed development was not observed.

It is claimed:

1. A new and distinct cultivar of *Clematis* plant named 'EviGsy155' as herein illustrated and described.

* * * * *